(12) United States Patent
Matheny

(10) Patent No.: US 6,328,757 B1
(45) Date of Patent: Dec. 11, 2001

(54) DEVICE AND METHOD FOR PERFORMING SURGERY WITHOUT IMPEDING ORGAN FUNCTION

(76) Inventor: Robert G. Matheny, 12746 Devon La., Carmel, IN (US) 46032

( * ) Notice: Subject to any disclaimer, the term of this patent is extended or adjusted under 35 U.S.C. 154(b) by 0 days.

(21) Appl. No.: 09/298,794

(22) Filed: Apr. 23, 1999

(51) Int. Cl.$^7$ ............................................. A61M 29/00
(52) U.S. Cl. ............................................................ 606/213
(58) Field of Search ........................... 606/213, 215, 606/190, 45; 604/174, 175; 600/204

(56) References Cited

U.S. PATENT DOCUMENTS

| | | | |
|---|---|---|---|
| 3,874,388 | 4/1975 | King et al. | 128/334 |
| 4,007,743 | 2/1977 | Blake | 128/334 |
| 4,836,204 | 6/1989 | Landymore et al. | 128/334 |
| 4,917,089 | 4/1990 | Sideris | 606/215 |
| 5,108,421 | 4/1992 | Fowler | 606/213 |
| 5,192,300 | 3/1993 | Fowler | 606/213 |
| 5,267,960 | * 12/1993 | Hayman et al. | 604/106 |
| 5,451,235 | 9/1995 | Lock et al. | 606/213 |
| 5,645,566 | * 7/1997 | Brenneman et al. | 606/213 |
| 5,709,707 | 1/1998 | Lock et al. | 606/213 |
| 5,716,367 | 2/1998 | Koike et al. | 606/144 |
| 5,741,234 | * 4/1998 | Aboul-Hosn | 604/174 |
| 5,797,960 | 8/1998 | Stevens et al. | 606/213 |
| 5,827,318 | * 10/1998 | Bonutti | 606/190 |
| 5,830,232 | * 11/1998 | Hasson | 606/213 |
| 5,871,474 | * 2/1999 | Hermann et al. | 604/256 |
| 5,938,660 | * 8/1999 | Swartz et al. | 606/45 |
| 5,944,697 | * 8/1999 | Biche | 604/174 |
| 5,951,588 | * 9/1999 | Moenning | 606/213 |

* cited by examiner

*Primary Examiner*—Cary E. O'Connor
(74) *Attorney, Agent, or Firm*—Woodard, Emhardt, Naughton, Moriarty & McNett (57) ABSTRACT

A method and device for enabling direct visualization and access to a body organ without impeding or stopping the function of the organ is provided. The device includes a balloon catheter, having a balloon at or near its distal end, and a preferably funnel-shaped access member positioned around the catheter. In use, an incision is placed in a patient, and a path is cleared to the organ or tissue on which surgery is to be performed. The catheter is inserted into the organ and to or through the tissue requiring treatment. If the catheter moves through the tissue to be treated, the balloon is inflated to provide a seal preventing fluids from moving through the tissue. The access member is then advanced over the catheter to the tissue site, enabling the surgeon to directly see and access the tissue.

30 Claims, 7 Drawing Sheets

DEVICE AND METHOD FOR PERFORMING SURGERY WITHOUT IMPEDING ORGAN FUNCTION

FIELD OF THE INVENTION

The present invention is in the field of surgical devices and methods for obtaining access to and visualizing a site where surgery or other treatment is needed. Specifically, the present invention contemplates a device and method for obtaining access to tissues within a body organ without impeding or stopping the function of that organ.

BACKGROUND OF THE INVENTION

In the field of surgery, two general methods of accessing a site within a patient's body are used. In open surgery, the patent is anesthetized, commonly with general anesthesia, and the surgeon then makes a relatively large incision in the patient. The location and size of the incision will, of course, depend on the organ or tissue to be treated, as well as the disease, injury, or other abnormality of such tissue. After the incision is made, the surgeon retracts the skin, muscle, fatty tissue, bones, or other tissue that lie between the incision and the treatment area or that otherwise hinder the surgeon's access to such area. The surgeon can then view the tissue to be treated, for example the heart, and can directly approach that tissue with surgical instruments. At this point, a surgeon may have to impede or stop the function of the organ or tissue to be treated. Most commonly, that step is necessary in order to prevent movement of the organ or tissue, or to prevent fluid flow into or out of the organ or tissue. Again using the heart as an example, open-heart surgery requires the surgeon to connect the patient's circulatory system to an external machine (a "heart-lung machine," or in the surgeon's vernacular a "pump"), and to induce cardioplegia. With the patient's blood routed around the heart and the heart muscle itself stationary, the heart surgeon can then enter the heart and perform the necessary operation.

The principal advantage of such open procedures is the comparative ease of access to the organ or other tissue to be treated. The organ or other tissue is substantially exposed to operating theater conditions, providing ample light on and space around the tissue, and aid the surgeon in performing the procedure. A significant disadvantage, however, is the necessity of stopping the function of the organ or tissue. In such cases, the risks of ischemic or other damage or irritation to the organ resulting from discontinuing of the organ's function organ are substantially heightened. Additionally, there is the risk that the organ or tissue will not restart its function or will restart only partially. In heart surgery cases, for example, other risks such as the risk of emboli being introduced into the vascular system is also increased. Further, the damage to tissues that are retracted or proximate to the incision in such open surgical procedures, and their concomitant discomfort and relatively long healing term, are also disadvantages of open surgical procedures.

The second general method of performing internal surgery is via intravascular or percutaneous minimally-invasive procedures. Using non-invasive measures such as x-ray, ultrasound, or other techniques or procedures, it is frequently unnecessary to expose the internal tissues of patients in order to diagnose or treat medical problems. Once a disease, injury, or abnormality has been non-invasively detected, one or more small incisions are made through the patient's skin, either in the neighborhood of the problem to be treated or to gain access to a relatively large blood vessel, such as the femoral vein. Specially-developed thin and commonly flexible instruments can then be inserted into the patient through the incision, maneuvered into position and the tissues can be treated using such instruments. Some procedures may be performed by observing the motion of the instruments relative to the tissues under fluoroscopy. In other procedures, a flexible observation device or endoscope may be inserted through an incision, and a view of the tissues to be treated may be obtained through the endoscope. When the procedure is completed, the instruments are withdrawn and the small incision(s) are closed.

Again taking the heart as one example, in the case of minimally-invasive heart treatments, a catheter may be introduced into a blood vessel percutaneously. The catheter can then be advanced under fluoroscopic observation within the blood vessel toward and into the heart. At that point, medication may be administered, or instruments and/or implants may be advanced through the catheter and utilized within the heart. Alternatively, as indicated in U.S. Pat. No. 5,797,960, a small thoracic incision can be made, and a cannula inserted through the small incision and a substantial portion of the chest and into the heart. Minimal-diameter instruments or implants can be advanced through the cannula and into the interior of the heart for employment.

Such minimally-invasive techniques have several advantages. First, the organ or tissue to be treated need not be stopped or impeded in order to treat it using such procedures. Additionally, because smaller incisions are used and there is less need for retraction of tissues proximate to the incision, there is less overall trauma and scarring to the tissues involved. Thus, a significant portion of the risks associated with currently-known open surgical procedures is not present with minimally-invasive procedures. Nonetheless, there are several disadvantages to minimally-invasive procedures as well. The principal disadvantage is the lack of direct access to and visualization of the organ or tissue that requires treatment. Minimally-invasive procedures are generally not directly observable, due to the small profiles of cannulas, catheters, and incisions used in such procedures. Fluoroscopic techniques provide some indirect view of the treatment, but generally produce an image that is not very sharp or exact. Insertion of an endoscope can provide a somewhat sharper image, but such instruments have a limited field of vision and must provide light by which to see. Therefore, both the observation end and the light source must be focused relatively closely on a certain area of tissue, and may interfere with treatment of the tissue.

What is needed, therefore, is a device and method for minimally-invasive use in surgical procedures that allows direct access to and visualization of an organ or tissue needing treatment, but that does not require the stoppage or impedance of function of the organ or tissue. Such a device should incorporate the advantages of minimally-invasive surgery, in that it minimizes tissue trauma as well. The devices should be useful in one or more organs, but should particularly be useful in the heart, in which open surgeries necessitate stopping the heart, and in which minimally-invasive surgery may not adequately correct the problem.

SUMMARY OF THE INVENTION

The present invention contemplates an apparatus for accessing and visualizing tissue within a human heart cavity while said heart is beating, comprising a surgically sterile walled member having a perimeter wall, a distal portion and a proximal portion, with the wall member being positioned during open heart surgery within a cut opening in an outer heart wall. A substantially blood tight seal is formed between the walled member and the heart wall to prevent exsanguination therebetween. The distal portion of the walled member forms a substantially blood tight seal with an interior portion of the heart to prevent exsanguination therebetween, and the walled member and the seals providing an access to the interior of the heart within the walled member for direct surgical access to the interior heart tissue during open heart surgery while the heart is beating with blood flow through the heart and outside of said wall member. The distal and proximal portions of said perimeter wall may be substantially circular, and the walled member may be configured generally in the shape of a funnel.

In one embodiment, a tubular member is included having at least one lumen therethrough positioned within the walled member. The tubular member can include a balloon, such as a foam balloon that expands generally perpendicular to the tubular member to a greater degree than it expands generally parallel to the tubular member, at the distal end of the tubular member.

The perimeter wall may have at least one opening therethrough, which can include a port. The walled member can also include a seal member and/or at least one hook connected to said distal portion. The walled member can also be transparent.

In another embodiment, the invention contemplates an apparatus for accessing and visualizing a septum having a defect within a heart while said heart is beating, comprising a surgically sterile walled member having a perimeter wall including a distal portion and a proximal portion, with the walled member being positioned during open heart surgery within a cut opening in an outer heart wall with a substantially blood tight seal between the walled member and the heart wall to prevent exsanguination therebetween. The distal portion forms a substantially blood tight seal with a portion of the septum around the defect to prevent exsanguination therebetween, and the walled member and the seals provide an access to the interior of the heart within the walled member for direct surgical access to the septum and the defect during open heart surgery while the heart is beating with blood flow through the heart and outside of said walled member. Further, a catheter having at least one lumen therethrough can be positioned within the walled member. The catheter preferably includes a balloon, such as a foam balloon at the distal end of said tubular member. The catheter can be positioned through the defect and the balloon in its expanded state forms a substantially blood tight seal with the septum to prevent exsanguination therebetween. The distal portion and the balloon may press a portion of the septum therebetween to provide the seals.

The present invention also contemplates a method for accessing and visualizing tissue within a heart while it is beating, comprising the steps of providing a surgically sterile walled member having a perimeter wall including a distal portion and a proximal portion; positioning the walled member during open heart surgery within a cut opening in an outer heart wall with a substantially blood tight seal between the walled member and the heart wall to prevent exsanguination therebetween; and forming a substantially blood tight seal between the distal portion of the walled member and an interior portion of the heart to prevent exsanguination therebetween, thereby providing an access to the interior of the heart within the walled member for direct surgical access to the interior heart tissue during open heart surgery while the heart is beating with blood flow through the heart and outside of said wall member. The method may further include providing a tubular member having at least one lumen therethrough and a balloon at the distal end of the tubular member, with the tubular member being positioned within the walled member, and/or medically treating the interior portion of the heart to which access is provided, such as surgically repairing a defect in a septum.

In one embodiment, the method of the present invention includes inserting a tubular member having at least one lumen therethrough and a balloon at the distal end of the tubular member into the cut opening and through the defect, expanding the balloon, and forming a substantially blood tight seal between the balloon and the septum to prevent exsanguination therebetween. Additionally, the step of pressing the septum between the walled member and the balloon to form the substantially blood tight seals can be performed.

The device and method of the present invention provides the advantage of direct access to and visualization of internal tissues, particularly those inside a body organ, with a less-invasive approach than open surgery and with the advantage of avoiding the arrest of the tissue or organ to be operated on.

DESCRIPTION OF THE PREFERRED EMBODIMENT

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein, being contemplated as would normally occur to one skilled in the art to which the invention relates.

Figures 1, 1A:
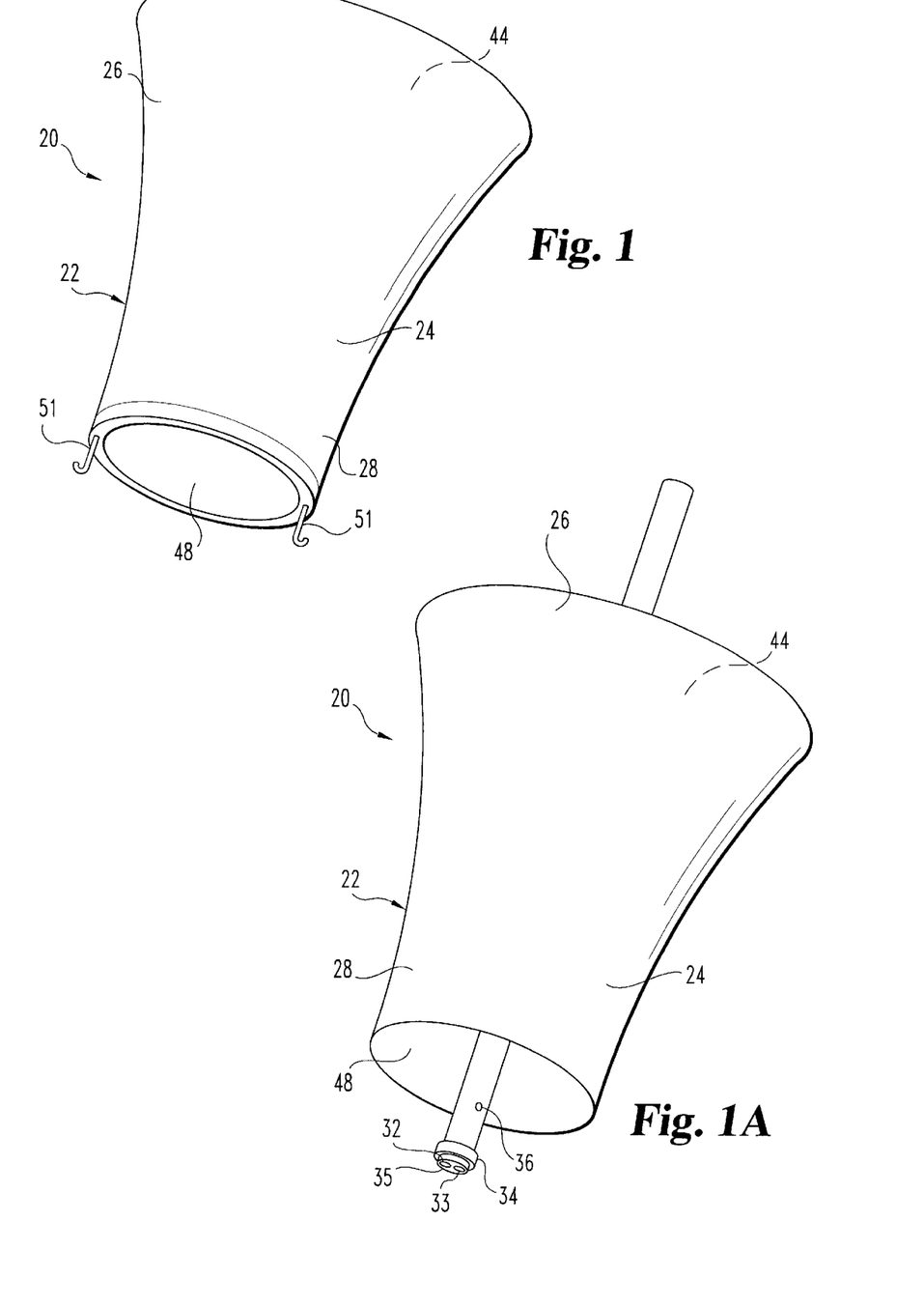
FIG. 1 is a perspective view of one embodiment of the apparatus of the present invention.
FIG. 1A is a perspective view of another embodiment of the apparatus of the present invention.
Figure 2:
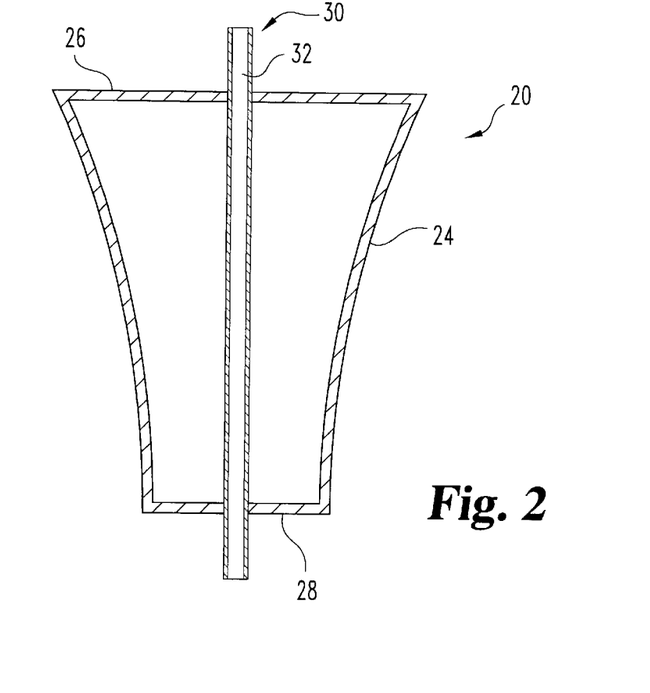
FIG. 2 is a cut-away view of the embodiment of the invention depicted in FIG. 1A.
Figure 3:
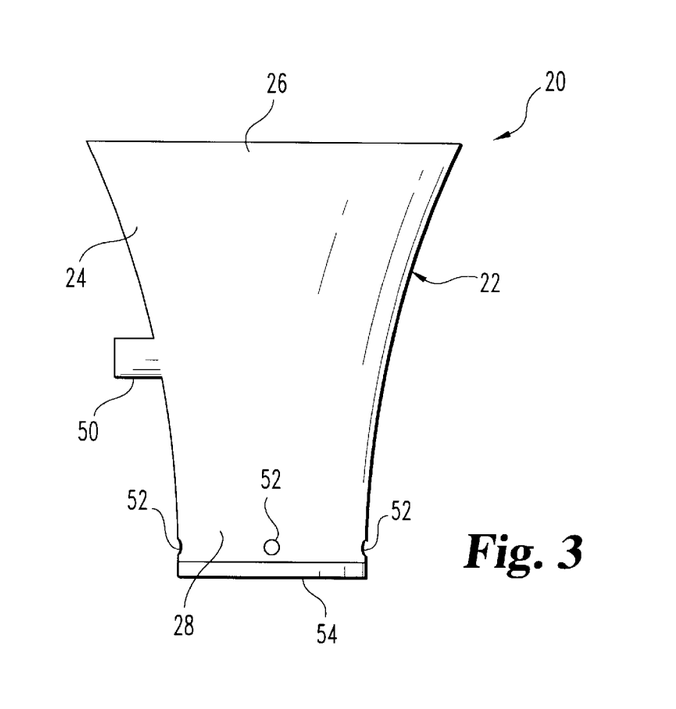
FIG. 3 is an alternate embodiment of the device of FIG. 1.

Referring generally to FIGS. 1–3, there is shown an embodiment of the surgical accessing and visualizing device 20 of the present invention. Device 20 includes walled member 22, having a perimeter wall 24 which includes a proximal portion 26 and a distal portion 28. Proximal portion 26 defines a proximal opening 44, and distal portion 28 defines a distal opening 48. Walled member 22 is sized and configured to be placed through an outer organ wall, for example an outer heart wall, so that a surgeon can directly view and operate on an interior portion of the organ through the walled member.

In the illustrated embodiment, device 20 is generally funnel-shaped; that is, proximal portion 26 and proximal opening 44 are larger than distal portion 28 and distal opening 48, respectively, and the inner dimension of device 20 narrows from proximal portion 26 toward distal portion 28. The inside of device 20 is preferably completely open between proximal opening 44 and distal opening 48. Device 20, in cross section roughly parallel to openings 44 and 48 as illustrated in FIG. 1, is roughly circular throughout. Other configurations, such as oval, square, or a regular polygon, may also be provided.

Figure 4A:
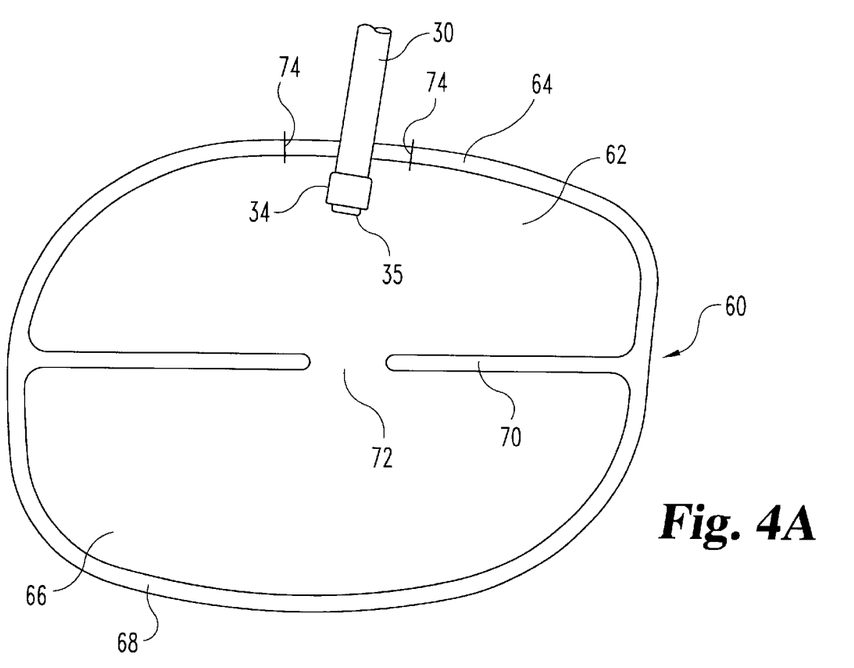
FIG. 4A is a cut-away view of a human heart, illustrating the use of the embodiment of the invention illustrated in FIG. 1A.
Figure 4B:
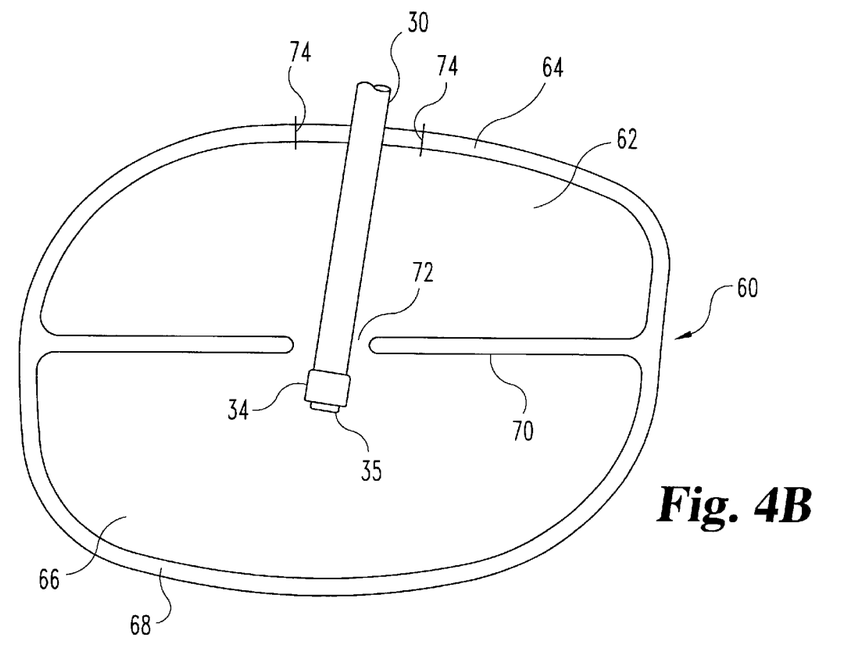
FIG. 4B is a cut-away view of a human heart as in FIG. 4A, showing further the use of the embodiment of the invention illustrated in FIG. 1A.
Figure 4C:
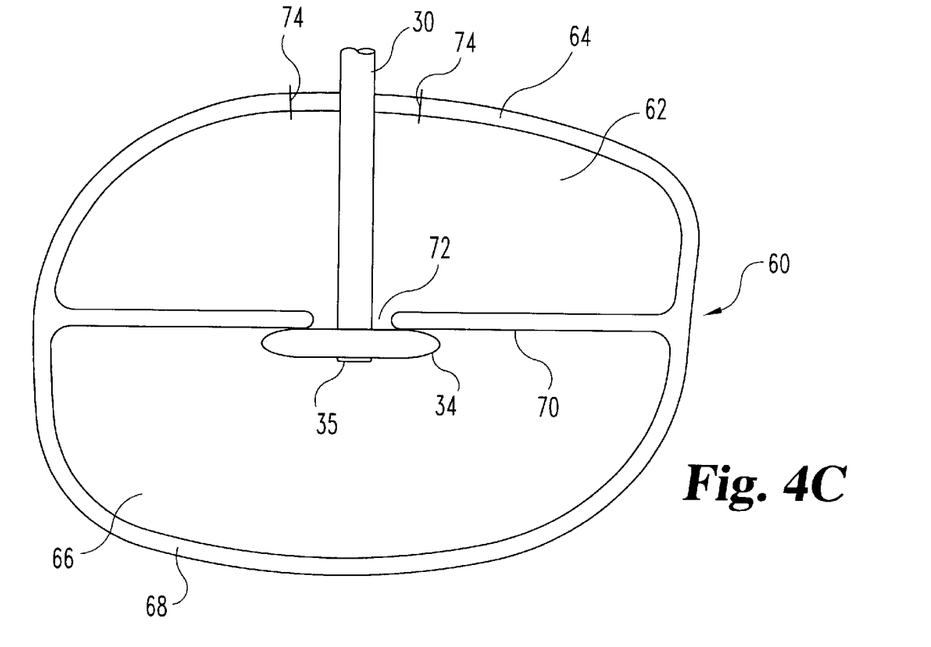
FIG. 4C is a cut-away view of a human heart as in FIG. 4A, further illustrating the use of the embodiment of the invention illustrated in FIG. 1A.
Figure 4D:
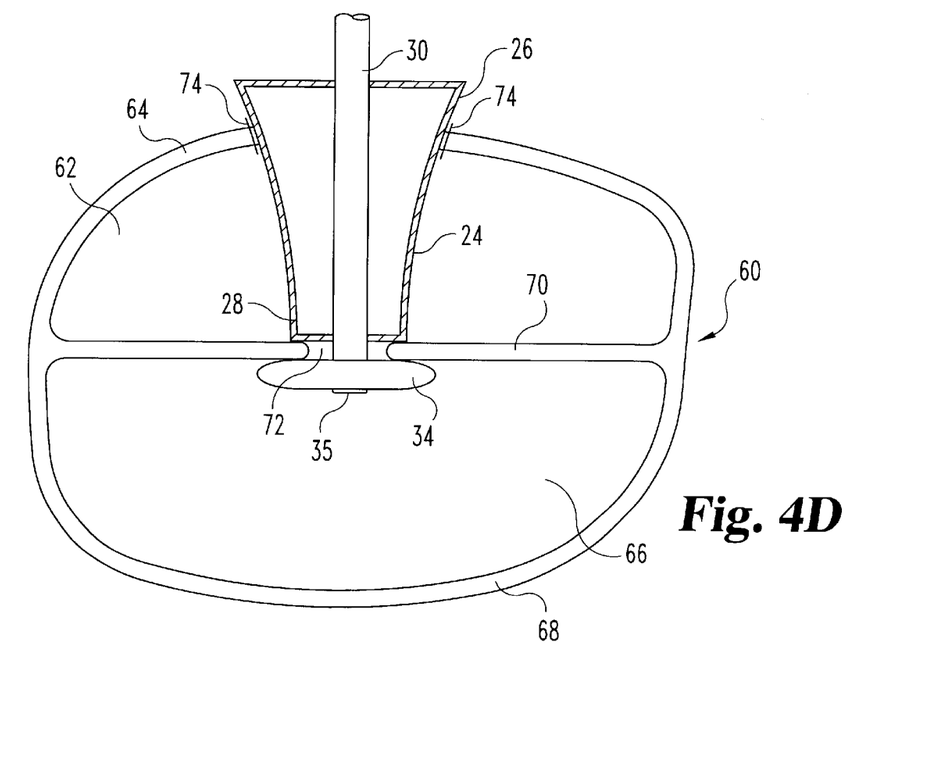
FIG. 4D is a cut-away view of a human heart as in FIG. 4A, further depicting the use of the embodiment of the invention illustrated in FIG. 1A.
Figure 4E:
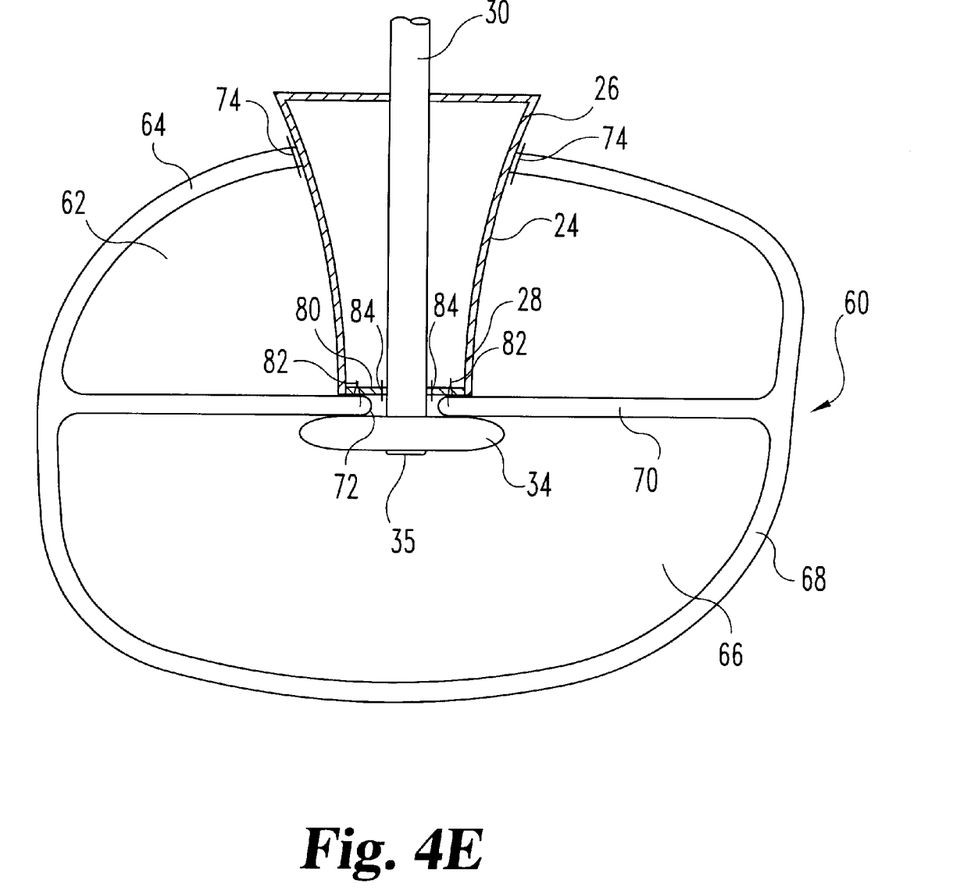
FIG. 4E is a cut-away view of a human heart as in FIG. 4A, further depicting the use of the embodiment of the invention illustrated in FIG. 1A.
Figure 5:
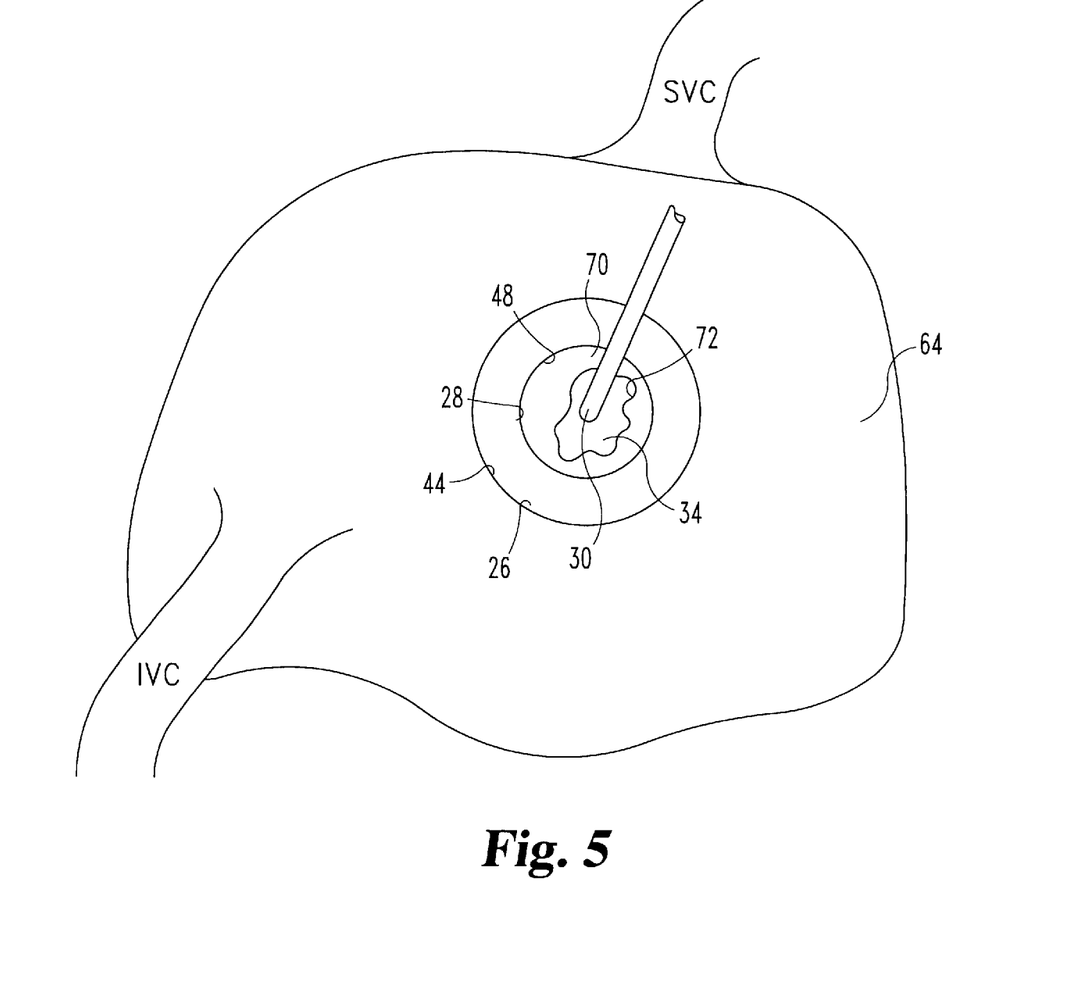
FIG. 5 is a side view of the right atrium of the human heart, further depicting the use of the embodiment of the invention illustrated in FIG. 1A.

Distal portion 28 is configured to form a substantially liquid-tight (e.g., blood-tight) seal with an interior portion of the organ on which the operation is to be performed (e.g., septum 70 of the heart 60 illustrated in FIGS. 4A–5). The part of distal portion 28 adjacent to distal opening 48 is preferably pressed against the interior portion to form the seal. Additionally, distal portion 28 may have a roughened surfaced to better grip and seal to the interior portion. Further, device 20 may be fitted with hooks or other fixation elements which allow it to be directly fixed to tissue. Hooks 51, in this alternate embodiment, are attached to distal portion 46, and may be adjacent to or within distal opening 48. As illustrated in FIG. 3, device 20 may also include a seal member 54 fixed circumferentially around distal portion 28 of device 20, and preferably directly adjacent to distal opening 48 of device 20. Seal member 54 can be made of natural or synthetic rubber or other suitable ceiling material, and when device 20 is used as described below, prevents leakage of fluids, particularly liquids, into the interior of device 20 through distal opening 48.

In an alternative embodiment, illustrated generally in FIG. 3, device 20 additionally includes a port 50, which provides access to the interior of device 20. Port 50 is tubular in the illustrated embodiment, and is preferably sized and configured for mating with standard medical or scientific tubing. Accordingly, port 50 may have a circular, oval, regularly polygonal, or other appropriate opening. Port 50 enables tubing to be connected to device 20, so that suction may be provided, or so that liquids, gases, catheter-guided instruments, and the like may be introduced into device 20. Port 50 may be integral with device 20, or may be a separate piece fitted into an aperture in the side of device 20. Port 50 may be placed in any position in device 20. If port 50 is intended for introducing matter into device 20, it may be advantageous to place port 50 at or near proximal portion 26 of device 20. Conversely, if suction of fluids is desired, port 50 may be placed at or near the distal portion 28 of device 20.

Additionally, in an alternate embodiment device 20 can include one or more apertures 52 in or adjacent to distal portion 28. Apertures 52 can be used with suction or otherwise to drain fluids that accumulate inside device 20. Also, apertures 52 may be used to allow carbon dioxide or other suitable gas from inside device 20 to diffuse into the area surrounding device 20 to prevent emboli or other dangerous or complicated medical situations.

Along with device 20, a flexible and/or expandable member may be included, which is to be used in a sealing relationship with the distal portion 28 of device 20. As used hereinafter, "flexible" is given a broad definition, and comprehends within its meaning the terms elastic, expandable and malleable. Referring generally to FIG. 2, there is shown an embodiment of the surgical accessing and visualizing device 20 of the present invention with a balloon catheter 30 placed within generally tubular visualization device 20.

Balloon catheter 30, in the illustrated embodiment, includes at least one lumen 32 through a substantial portion of the length of balloon catheter 30. Balloon catheter 30 also includes a flexible and expandable balloon member 34 that may or may not communicate with lumen 32. Balloon member 34, in a particular embodiment, is placed at or near the distal end 35 of balloon catheter 30. Balloon member 34 may be of any of a variety of constructions known in the art, such as a gas- or fluid-expandable balloon. Most preferably, balloon member 34 is a foam-filled balloon member having the rough shape of a circular disc (see FIGS. 4C and 4D) in its expanded state, and which contracts to a substantially smaller roughly circular disc (see FIG. 2) when suction is applied. Balloon catheter 30 may also include a radiopaque portion 35 to assist in its placement, as described below.

Balloon catheter 30, in an alternate embodiment, includes an aperture 36 which communicates with lumen 32 of balloon catheter 30. Lumen 32 and aperture 36 can be utilized to drain fluids from an anatomical site in which device 20 is being used. Alternately, lumen 32 and aperture 36 can be used to introduce gases, fluids, medicaments, or other agents into the anatomical site in which device 20 is being used. In an embodiment in which balloon catheter 30 includes aperture 36, and further includes balloon member 34 which requires a fluid (liquid or gaseous) communication between balloon member 34 and a fluid source (not shown), balloon catheter 30 should include at least two lumens, one in fluid connection with aperture 36, and one in fluid connection with balloon member 34.

Surgical accessing and visualizing device 20 may be used in any surgical procedure in which it is desired to have direct access to an internal organ, or to an internal portion of an organ. Device 20 is placed through the tissue of an internal organ so that distal portion 46 and distal opening 48 are adjacent to or in contact with tissue to be surgically treated, while proximal portion 42 and proximal opening 44 remains outside the internal organ so that the surgeon can directly examine and perform the desired procedure on the desired tissue site.

Device 20 may be used with any hollow organ, among others, and especially with hollow organs having a relatively high volume of fluid within and/or fluid flow through the organ. Device 20 is especially useful in correcting certain diseases, injuries, malformations, or other defects of the heart, such as atrial septal defect, atrial septal aneurysm, patent foramen, and atrial myxoma. Visualizing device 20 can also be used to provide clearer visualization and access during electrophysical ablation of vascular and/or cardiac pathways, or during angioscopy procedures.

The general use of surgical access and visualizing device 20 is as follows with particular reference to repair of an atrial septal defect. Referring generally to FIGS. 4A–5, in which a schematic view from the top of a heart 60 is shown, heart 60 includes a right atrium 62 having a right atrium wall 64, and a left atrium 66 having a left atrium wall 68. Between right atrium 62 and left atrium 66, there is a septum 70 which generally separates atria 62 and 66 into their respective separate chambers. As illustrated in FIGS. 4A–5, septum 70 is malformed in that it has an atrial septal defect 72, which is an aperture through septum 70 that allows the abnormal flow of blood between atria 62 and 66 to occur.

To repair atrial septal defect 72 through use of accessing and visualizing device 20, the patient is first anesthetized, and a mini-thoracotomy is made. It is believed that two modes of access to the heart are most preferable, those being (1) via a relatively small incision under the patient's breast, or (2) via a sternotomy. Other incision sites, however, may be used depending on the organ or problem to be treated, or on the surgeon's preference or experience. Once the incision is made, tissues are retracted as necessary in order to obtain a view of and access to the heart.

An incision is then made in an atrium wall, e.g., right atrium wall 64 in FIGS. 4A–4D. Through that incision, balloon catheter 30 is introduced into right atrium 62. Stitching, such as a conventional purse-string suture 74, may be placed around the incision and balloon catheter 30 so as to inhibit or minimize loss of blood therethrough.

Balloon catheter 30 is advanced through right atrium 62 and through atrial septal defect 72 and into left atrium 66. This procedure may be performed under x-ray viewing, fluoroscopy, ultrasound, or other known ways of observing relative movement inside a closed bodily system. Balloon catheter 30 is advanced through atrial septal defect 72 to at least a position in which balloon member 34 is entirely clear of atrial septal defect 72. Balloon member 34 is then expanded. Balloon member 34 should either be chosen to have a size and configuration after expansion to cover the entirety of atrial septal defect 72, or should be variably expandable, and should be expanded at least to a size to completely cover atrial septal defect 72. After expansion of balloon member 34, balloon catheter 30 may be retracted so that balloon member 34 is in approximately fluid-tight contact with the portion of septum 70 surrounding the circumference of atrial septal defect 72.

When the fluid-tight connection between balloon member 34 and septum 70 has been attained, device 20 is introduced over balloon catheter 30. When distal portion 46 is in contact with or adjacent to right atrium wall 64, purse-string sutures 74 are loosened. The incision surrounded by purse-string sutures 74 is then opened, distal portion 28 of device 20 is inserted through the incision, and purse-string sutures 74 are re-tightened around device 20. Device 20 is advanced until distal portion 28 contacts septum 70 and such that distal opening 48 encircles atrial septal defect 72, and a substantially blood-tight seal is formed between distal portion 28 and septum 70. Device 20 may be pressed further against septum 70 to establish or improve the seal therebetween, and/or balloon member 34 of balloon catheter 30 may be further drawn toward septum 70 and distal portion 28 in order to ensure the best possible seals between balloon member 34 and septum 70, and distal portion 46 and septum 70. Alternatively, in the embodiment of device 20 including hooks 51 attached to distal portion 46, as device 20 is advanced against septum 70, hooks 51 penetrate such tissue, thereby fixing device 20 to such tissue.

After device 20 is in place, direct viewing of and surgical access to septum 70 is possible through openings 44 and 48 of device 20. To repair atrial septal defect 72, a patch 80 can be introduced into the interior of device 20. Patch 80 may be introduced over balloon catheter 30, or may be separately introduced into device 20 by the surgeon. Patch 80 preferably has a small hole or slit, which allows patch 80 to be introduced over balloon catheter 30 or placed around balloon catheter 30 in contact with septum 70. After patch 80 is placed in contact with septum 70 so that it covers atrial septal defect 72, patch 80 is attached to septum 70 (and if patch 80 includes a hole or slit therein, the hole or slit is closed by purse-string suturing or other manner), thereby repairing atrial septal defect 72. The attachment can occur in a variety of ways, as for example by suturing, stapling, hooking, or implanting, or by other methods. Also, defect 72 may be stitched closed without a patch, as is known in the art. FIG. 4E depicts patch 80 being attached to septum 70 via sutures 82.

When patch 80 is secured to septum 70, balloon member 34 is deflated, and balloon catheter 30 and device 20 are removed, separately or simultaneously. Additional suturing or other closing or repair to patch 80 or septum 70 can be performed, if indicated. Purse-string sutures 74 are then tightened to close the incision through which access device 20 was inserted, and further sutures or other repair may be applied to atrium wall 64. The main thoracotomy is then closed.

As noted above, the visualizing and access device 20 of the present invention is particularly useful in treating or repairing the interior tissues of the heart. Access to the heart from the left side (e.g., through the left atrium) can be performed using device 20 as well as access from the right side, as described above. Further, device 20 can be used in any hollow organ having inner tissues or surfaces needing surgery or other treatment. Use of balloon catheter 30 as described above is particularly preferred for visualizing and repairing an atrial septal defect, but may be unnecessary when device 20 is used to visualize and access solid or unperforated tissues. For example, device 20 could be inserted through atrial wall 64 and a seal formed between atrial wall 64 and device 20 as described above, and distal portion 28 of device 20 could be placed and/or pressed in contact with solid or unperforated tissue. The seal formed between distal portion 28 and such solid or unperforated tissue would be sufficient to prevent or minimize exsanguination, since no perforation or defect would allow fluid into device 20.

Device 20 is preferably made of a sturdy plastic or metal, although other natural or synthetic materials could be used. Device 20 may be generally in the range of 3–5 centimeters in height (i.e., between proximal opening 44 and distal opening 48). The diameter of proximal opening 44 and distal opening 48 may be approximately 5–10 centimeters and 2–5 centimeters, respectively. Differing sizes of device 20, both in height and in the diameters of openings 44 and 48, are contemplated so that device 20 is well-suited to a patient's particular anatomy and problem to be corrected. For example, a child may require a device 20 which is smaller in height than a device 20 intended for an adult, and a patient having a smaller area of tissue to be visualized should receive a device 20 having a smaller distal opening 48.

Balloon catheter 30, as noted above, may be any of a number of known balloon catheters, or may be one specifically designed for use with device 20. Specifically, a foam balloon catheter, in which the foam is in an expanded state without external force being applied to it, and may be contracted through the application of suction or vacuum, is preferred. Further, the balloon member 34 preferably expands and contracts substantially in a plane perpendicular to balloon catheter 30. A balloon catheter that is currently preferred for use with device 20 is the foam balloon catheter manufactured by Bavona Corporation, model number 800-160, part number 800-165.

Flexible members other than balloon member 34 are also contemplated in the present invention, used either with or without a catheter. For example, a flexible member in the shape of a disc or shield may be deployed on the left atrial side of septum 70. Such a flexible member may be held against septum 70 to cover defect 72 in any of a variety of ways, such as by suction, adhesive or piercing fixation, or by pressing or holding against septum 70 using an implement. Further, the flexible member can have any of a number of two-dimensional or three-dimensional configurations so long as it covers defect 72, and can be made of any of a variety of materials, such as plastic, natural or synthetic rubber, nitinol or other shape-memory materials, or other appropriate substances. Introduction of the flexible member can occur in a number of ways, including direct placement or introduction via a catheter or other tubular member.

Figure 6A:
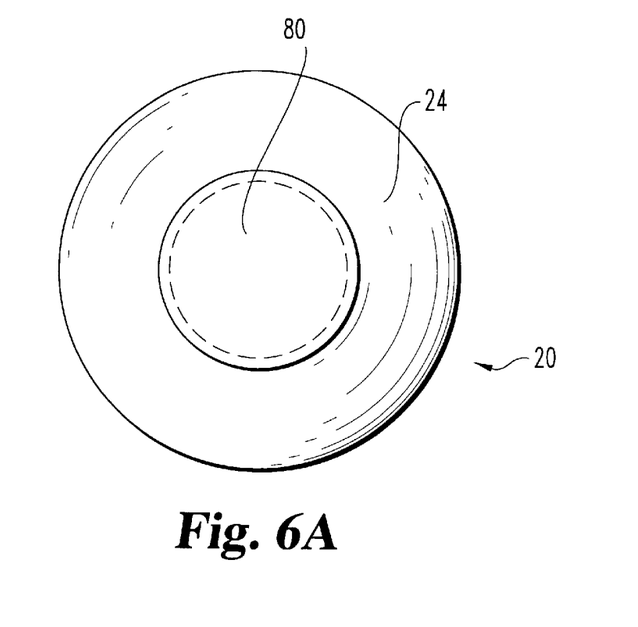
FIG. 6A is a bottom view of an embodiment of the apparatus of the invention.
Figure 6B:
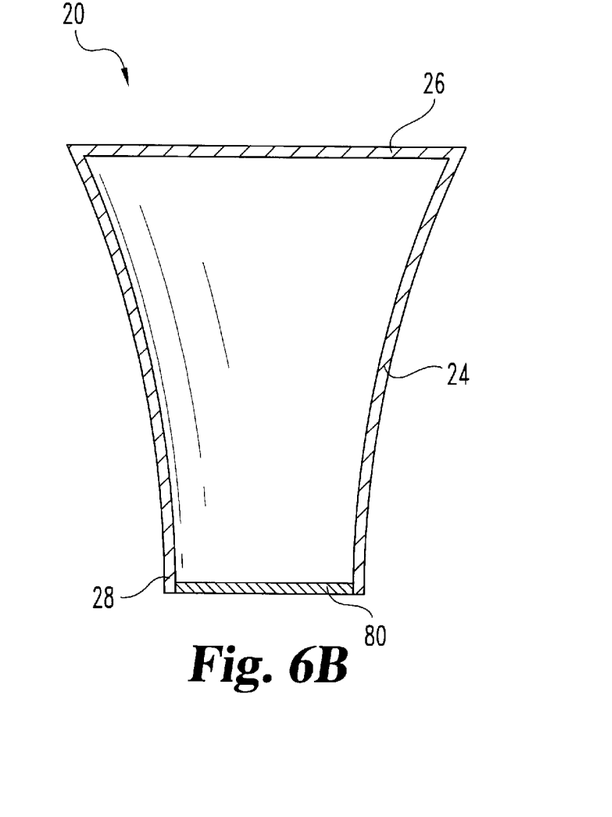
FIG. 6B is a cut-away view of the embodiment of the apparatus of the invention depicted in FIG. 6A.

In another alternative embodiment of device 20 illustrated in FIGS. 6A and 6B, patch 80 may be removably attached to device 20. Patch 80 may be attached to the inside or outside of distal portion 46 of tubular access member 40, and patch 80 should cover distal opening 48. Patch 80 may be attached to device 20 by adhesives or other known methods, and may include perforations to enable patch 80 to be easily detached from device 20. In use, device 20 with attached patch 80 is placed in the organ, e.g., the heart, as described above. After access device 20 is in place, stitches may be placed through patch 80 and into septum 70 to close atrial septal defect 72. Then patch 80 may be detached from tubular access member 40 by trimming with a scalpel or other appropriate cutting object, or by detaching at perforations if patch 80 is so equipped. Device 20 is then withdrawn and the surgery concluded, as described above.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. An apparatus for accessing and visualizing tissue within a human heart cavity while said heart is beating, comprising:
    a first sealing member comprising a circumferential surgically sterile walled member and a base; said base having an orifice, wherein said first walled member circumferentially forms a first seal through a first heart wall while simultaneously abutting said base against a heart septum forming a second seal with the base;
    said walled member being positionable during open heart surgery within a cut opening in an outer heart wall and adapted for a substantially blood tight first seal between said walled member and the outer heart wall tissue to prevent exsanguination therebetween;
    said base adapted for forming said substantially blood tight second seal with interior heart tissue which is separate from said outer heart wall tissue, said second seal being separate and distal from said first seal, said second seal being adapted for sealing with an interior portion of the heart to prevent exsanguination therebetween;
    said walled member and said first and second seals providing an access to the interior of the heart within said walled member for direct surgical access to the interior heart tissue during open heart surgery while the heart is beating with blood flow through the heart and outside of said walled member.

2. The apparatus of claim 1 wherein said walled member and said base are substantially circular.

3. The apparatus of claim 2 wherein said walled member is configured generally in the shape of a funnel.

4. The apparatus of claim 1, further comprising a flexible member positionable opposite said base such that said interior portion of the heart is between said flexible member and said base, said flexible member adapted for forming said substantially blood tight second seal with said interior portion of the heart.

5. The apparatus of claim 4, wherein said flexible member is a synthetic or nitinol disc.

6. The apparatus of claim 4, wherein said flexible member is a balloon.

7. The apparatus of claim 6, further comprising a tubular member having at least one lumen therethrough positioned within said walled member and in fluid connection with said balloon.

8. The apparatus of claim 7 wherein said balloon is a foam balloon.

9. The apparatus of claim 8 wherein said balloon expands generally perpendicular to said tubular member to a greater degree than it expands generally parallel to said tubular member.

10. The apparatus of claim 1, wherein said walled member has an opening therethrough.

11. The apparatus of claim 10, wherein said opening includes a port.

12. The apparatus of claim 1, wherein said walled member includes a seal member connected to said distal portion.

13. The apparatus of claim 1, wherein said walled member includes at least one hook connected to said distal portion.

14. The apparatus of claim 1, wherein said walled member is transparent.

15. An apparatus for accessing and visualizing a septum having a defect within a heart while said heart is beating, comprising:
    a first sealing member comprising a circumferential surgically sterile walled member and a base; said base having an orifice, wherein said walled member circumferentially forms a first seal through a first heart wall while simultaneously abutting said base against a heart septum, and a second sealing member exiting from said orifice forming a second seal with the base;
    said walled member being positionable during open heart surgery within a cut opening in an outer heart wall and adapted for a substantially blood tight first seal between said walled member and outer heart wall tissue to prevent exsanguination therebetween;
    said base adapted for forming said substantially blood tight second seal with interior heart tissue which is separate from said outer heart wall tissue, said second seal being separate and distal from said first seal, said second seal being adapted for sealing with a portion of the septum around the defect to prevent exsanguination therebetween;
    a flexible member having an expanded state and an unexpanded state, said flexible member being positionable on the side of the septum opposite said base and adapted for contacting the septum in its expanded state to form a substantially blood tight seal around the defect to prevent exsanguination therebetween;
    said walled member and said first and second seals providing an access to the interior of the heart within said walled member for direct surgical access to the septum and the defect during open heart surgery while the heart is beating with blood flow through the heart and outside of said walled member.

16. The apparatus of claim 15, further comprising a catheter having at least one lumen therethrough positioned within said walled member.

17. The apparatus of claim 16, wherein said flexible member is a synthetic or nitinol disc, said disc being capable of being passed through said lumen in the unexpanded state and capable of covering the area of the defect in the expanded state.

18. The apparatus of claim 16 wherein said flexible member is a balloon at the distal end of said catheter capable of covering the area of the defect in the expanded state.

19. The apparatus of claim 18 wherein said balloon is a foam balloon.

20. The apparatus of claim 19 wherein said catheter is positionable through the defect.

21. The apparatus of claim 15 wherein said sealing member includes a patch detachably connected to said base.

22. A method for accessing and visualizing tissue within a heart while said heart is beating, comprising the steps of:

providing a first sealing member comprising a circumferential walled member and a base; said base having an orifice, wherein said first walled member is circumferentially adapted for forming a first seal through a first heart wall while simultaneously abutting said base against a heart septum forming a second seal with the base;

positioning said walled member during open heart surgery within a cut opening in an outer heart wall to form a substantially blood tight first seal between said walled member and outer heart wall tissue to prevent exsanguination therebetween; and forming a substantially blood tight second seal with interior heart tissue which is separate from said outer heart wall tissue, said second seal being formed between said base and an interior portion of the heart to prevent exsanguination therebetween;

thereby providing an access to the interior of the heart within said walled member for direct surgical access to the interior heart tissue during open heart surgery while the heart is beating with blood flow through the heart and outside of said wall member.

23. The method of claim 22, further comprising;

providing a flexible member having an expanded and an unexpanded state;

positioning said flexible member opposite said base in the unexpanded state such that said interior portion of the heart is between said flexible member and said base; and expanding said flexible member to form a substantially blood tight seal with said interior portion of the heart.

24. The method of claim 23, further comprising:

providing a tubular member having at least one lumen therethrough and introducing said flexible member in the unexpanded state into the body via said lumen.

25. The method of claim 23, further comprising providing a tubular member having at least one lumen therethrough, wherein said flexible member is a balloon in fluid connection with said lumen, and positioning said tubular member within said walled member.

26. The method of claim 22, further comprising:

medically treating the interior portion of the heart to which access is provided.

27. The method of claim 26, wherein said interior portion is a septum having a defect, and wherein said treating step includes surgically repairing said defect.

28. The method of claim 27, further comprising:

inserting a tubular member having at least one lumen therethrough and a balloon at the distal end of said tubular member into said cut opening and through said defect;

expanding said balloon; and forming a substantially blood tight seal between said balloon and said septum to prevent exsanguination therebetween.

29. The apparatus of claim 1, comprising a second sealing member exiting from said orifice.

30. The method of claim 22, comprising the step of exiting a second sealing member from said orifice.

* * * * *